US006440912B2

(12) United States Patent
McGee et al.

(10) Patent No.: US 6,440,912 B2
(45) Date of Patent: *Aug. 27, 2002

(54) POST FOAMING SHOWER GEL

(75) Inventors: Thomas McGee, Orangeburg, NY (US); Reuven Sarraf, Teaneck, NJ (US); Steven Semoff, West Nyack, NY (US)

(73) Assignee: Givaudan SA (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/384,755

(22) Filed: Aug. 27, 1999

Related U.S. Application Data
(60) Provisional application No. 60/115,826, filed on Jan. 14, 1999, and provisional application No. 60/098,088, filed on Aug. 27, 1998.

(51) Int. Cl.7 ............................................. C11D 17/04
(52) U.S. Cl. ........................ 510/140; 510/158; 510/403; 510/406
(58) Field of Search ................................ 510/140, 158, 510/403, 406

(56) References Cited

U.S. PATENT DOCUMENTS 3,378,169 A * 4/1968 Clark .......................... 222/95
3,541,581 A * 11/1970 Monson ........................ 424/47
3,735,785 A * 5/1973 Nigrd .......................... 141/20
4,271,991 A * 6/1981 Diamond .................... 222/389
4,431,120 A * 2/1984 Burger ........................ 222/192
4,772,427 A 9/1988 Dawson et al. ............. 510/158
5,248,495 A * 9/1993 Patterson et al. ............. 424/73
5,308,643 A * 5/1994 Osipow et al. ................ 424/43
5,334,325 A 8/1994 Chaussee ............... 252/174.16
5,560,859 A 10/1996 Hartmann et al. .......... 510/135
5,602,091 A * 2/1997 Monson et al. ............. 510/406
5,902,225 A * 5/1999 Monson ....................... 516/10
5,902,778 A * 5/1999 Hartmann et al. .......... 510/135
5,962,396 A * 10/1999 Pollack et al. .............. 510/433

FOREIGN PATENT DOCUMENTS

| WO | WO 94/02109 | | 2/1994 |
| WO | WO 97/03646 | | 2/1997 |
| WO | 97/03646 | * | 2/1999 |

* cited by examiner

Primary Examiner—Lorna M. Douyon
(74) Attorney, Agent, or Firm—Fish & Richardson P.C.

(57) ABSTRACT

A post-foaming composition in combination with a dispenser adapted to dispense a fine stream of the composition onto skin that foams upon contact. The composition contains a material which is a volatile liquid at atmospheric pressure and between 5%–50% w/w surfactant solids. The composition may be dispensed as a mist, foam, gel or liquid at a rate between 0.5 grams/sec and 10 grams/sec.

18 Claims, 5 Drawing Sheets

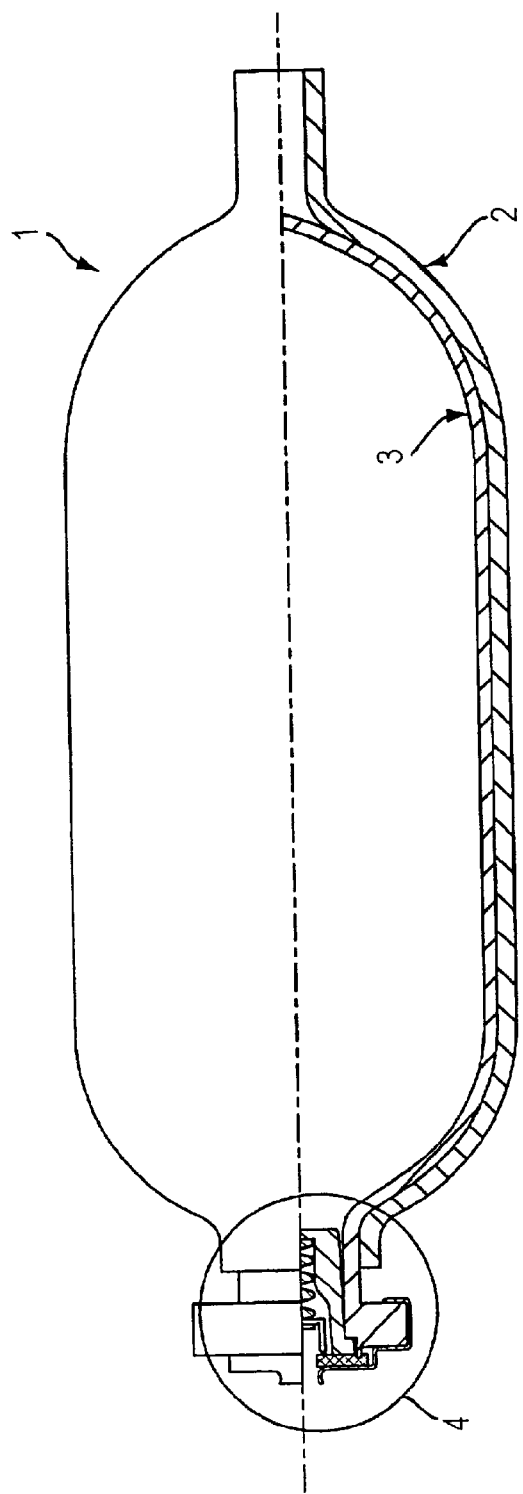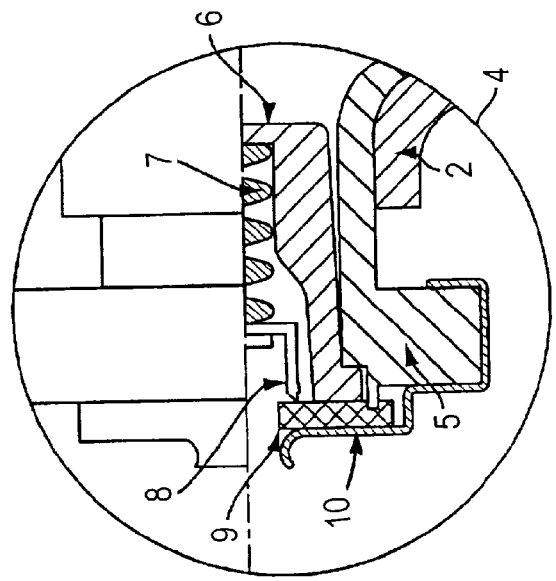

POST FOAMING SHOWER GEL

This application claims priority from Provisional application Ser. No. 60/115,826, filed Jan. 14, 1999, which claims priority from Provisional application Ser. No. 60/098,088, filed Aug. 27, 1998.

FIELD OF THE INVENTION

The present invention relates to a post foaming bodywash or shower gel. The bodywash is contained in a container having an actuator system for dispensing the bodywash. The post foaming bodywash formulation may be applied to skin as a fine stream gel which foams upon contact with skin. The gel which foams upon contact with the skin is dispensed from the container by manipulation of the actuator system.

BACKGROUND OF THE INVENTION

Conventional skin cleansing liquid products and shower gels, are usually thick liquids, packed in bottles, which are relatively slow foaming and produce very little, relatively weak foam which quickly flattens after release from the bottle. Post-foaming gels such as shaving gels, use a soap-based system which may optionally contain a minor amount of a surfactant. Prior art post-foaming gel shower products have conventionally thickened sodium lauryl ether sulfate and fatty acid diethanolamide blended together with a low level of foaming agent, such as the liquefied hydrocarbon and chlorofluorohydrocarbon propellants. A number of major problems are associated with this type of product.

Bodywash products currently available have many drawbacks. For example, they are stringy, tacky to the touch. In addition, they possess very poor high temperature stability, are restricted to very low foaming agents, and require high viscosity bases to allow for thinning effects on the base while still trying to achieve a good gel. Standard shower gels also fail to provide enough deep cleaning capabilities and leave a greasy and slimy feeling and also are filmy to the touch. They also fail to stick to skin and lather in place.

The shower gel market presently contains the following product forms: clear and opacified/pearlized liquids, clear and opacified/pearlized gels, liquid/gels with suspended materials (encapsulated moisturizers, vitamins, botanicals), super fatted bases and multiphase bases.

For example, Hartmann, et al., U.S. Pat. No. 5,560,859 discloses a post-forming gel shaving composition which contains from about 40 to about 90 percent by weight water; from about 4 to about 25 percent by weight water-soluble soap; from about 0.5 to about 12 percent by weight aliphatic liquid post-foaming agent having saturated aliphatic hydrocarbons; from about 0.01 to about 5 percent by weight of at least one water-soluble gelling agent forming in the composition a gel having a yield value sufficiently high to restrain the composition from foaming for at least about 60 seconds; and from about 0.1 to about 2 percent by weight of a poly(ethylene oxide) having an average molecular weight of at least $2 \times 10^5$.

Dawson, et al., U.S. Pat. No. 4,772,427, discloses a stable, post-forming gel shower product having a soap-free, surfactant-based gel composition which includes a major amount of water, about 3–23% by weight of a water-soluble anionic alkali metal $C_{10}$–$C_{16}$ alkyl ether sulfate surfactant, about 1–24% by weight of a water dispersible ethoxylated fatty alcohol or fatty ester, about 2–4% of isopropyl myristate, about 1–10% of a mono- or disaccharide and about 5–20% by weight of a saturated aliphatic hydrocarbon foaming agent having 4 to 5 carbon atoms as an integral part of the gel structure, the anionic surfactant and the ethoxylated fatty alcohol or ester being present in a weight ration of 4:1 to about 1:4. Each of these documents, in particular the detailed description and examples, are incorporated by reference herein as set forth in their entirety.

Moreover, applicators which are conventionally employed for delivering the bodywash products on the market today are typically designed for pumping, pouring or squeezing the product from the applicator.

Thus, despite the products which are currently available, there is still a need for a composition containing a surfactant system which is non-greasy, refreshing, deep cleaning, and foams upon contact with skin and therefore eliminates the need to use applicators which require manual secondary applicators to generate foam in a bodywash or gel.

Surprisingly, it has now been found that the aforementioned problems and limitations associated with the bodywash liquids and shower gels available on the market today, are overcome by the present novel post-foaming composition which is employed in combination with a unique dispenser adapted to dispense a fine stream of the composition, which foams upon contact with the skin.

SUMMARY OF THE INVENTIONS

The present composition of the invention, packaging and actuator design produces a bodywash having very high esthetic values, including moisturizing capabilities which aid in producing soft skin without the greasy, slimy, filmy feeling frequently associated with hand creams; a refreshing, substantive fragrance instead of the perfumey fragrances usually associated with known bodywashes; and the present bodywash composition is applied directly to the skin instead of using a pouf as is usually done with known bodywashes.

Thus, the present invention also provides a post-foaming composition in combination with a dispenser that is adapted to dispense a fine stream of the post-foaming composition. The composition includes at least one surfactant and a material which is a volatile liquid at normal, i.e., atmospheric, pressure and foams upon contact with skin. The combination of the composition ingredients and the unique dispenser enables the user to deploy the fine stream of the composition onto the skin facilitates the immediate foaming of the composition. The composition is formulated to adhere to skin and not drip or run in a highly humid environment.

DETAILED DESCRIPTION OF THE INVENTIONS

The post foaming composition of the present invention includes at least one surfactant and a material which is a volatile fluid such as a liquid at normal, i.e., atmospheric, pressure. The composition foams upon contact with the skin.

In one embodiment, the volatile fluid may be a liquid hydrocarbon. The hydrocarbon liquid may be small and/or medium length chain hydrocarbons, or may be small and medium chain halogen substituted carbon chains. More particularly, the volatile liquid may be a carbon compound comprising or selected from the group consisting of propane, n-butane, isopentane, incompletely halogenated chlorofluoro carbons and dimethyl ether and/or mixtures thereof. Preferably, the hydrocarbon is a 5 carbon aliphatic hydrocarbon.

The bodywash liquids and shower gels of the invention are, generally, aqueous solutions which may contain anionic surfactants, nonionic surfactants, soaps, Theological agents, conditioners, humectants, moisturizers, preservatives, botanical extracts, vitamins, fragrance and/or color. Other chemical formulas with unique skin care benefits, such as cationic or polyquaterniums, may also be added.

A shower gel composition of the present invention preferably contains 5%–30% w/w solids with a pH range between 4.0–7.5 and has a viscosity range from 1000 cps–60,000 cps. The shower gel composition may contain from 14.85% (wt) to 42.35% (wt) of water. The composition of the present invention may contain a post foaming additional agent such as a volatile liquid in an amount of at least 0.5% w/w of the volatile liquid between 1%–10% w/w of the volatile liquid. More preferably, the composition may contain less than 7.5% w/w of the volatile liquid. Most preferably from about 1% to about 5%. The volatile liquid contributes to the foaming action of the composition.

The post-foaming composition of the present invention may have a viscosity range of from about 1,000 cps to about 15,000 cps, with a preferred range of between about 2,000 cps to about 5,000 cps. The active ingredient level or solids content for this formula may range from about 5% to about 50%, preferably from about 5% to about 25%, or from about 10% to about 25%, with a preferred range of from about 15% to about 20%. The ratio of principle anionic surfactant to coactives is about 7.5 to about 1.

This composition when dispensed from the dispenser will dose as a clear gel/liquid and transform into a soft highly reticulated foam upon contact with skin.

The viscosity of the base concentrate is suitable for rapid blending with the post-foaming additive. A Theological change occurs when the hydrocarbon post-foaming agent is mixed with the composition base concentrate. This combination produces a clear liquid or an opaque paste. Different combinations of the elements of the composition, of course, may also be possible. The composition base may include an alkyl sulfate salt, an isoethionate, a betaine and an acrylic acid copolymer. These components may be blended in different ratios. Different ratios of elements will result in a broad range of viscosities when mixed with the hydrocarbon post foaming agent.

Bodywash liquids or shower gels are aqueous solutions which may contain anionic surfactants, nonionic surfactants, soaps, Theological agents, conditioners, humectants, moisturizers, preservatives, botanical extracts, vitamins, fragrance and/or color. Other chemical specialties with unique skin care benefits such as cationic or polyquaterniums may also be added. The composition of the present invention is used in combination with a dispenser which is adapted to dispense a fine stream of the composition onto skin. The dispenser may have an orifice which is less than about 0.020 inches in diameter, and preferably less than about 0.025 inches in diameter. The orifice may also have a length which is less than about 0.5 inches in length, and preferably about 0.25 inches in length.

It is the combination of the formulation of the composition and the delivery of the composition by the dispenser that produces an unique composition that foams upon contact with the skin and is an excellent bodywash.

The package componentry is extremely important and involves developing a system that will deliver a product as a clear liquid/gel that will foam upon contact with the skin. The final products should dispense as a fine stream and the entire contents of the container should evacuate at the same spray rate and pattern.

The actuator design (orifice size and nozzle length) must be optimized in conjunction with the viscosity of the base composition such that there is no change in the characteristics of the product during the products' usage.

In order to deliver a consistent dosage foam, it was determined that a clear low viscosity liquid that immediately blows into foam is optimal. It is important that mixing of the base/post-foaming agent occur quickly so that the product would not run upon contact with the skin. In fact, the final product density and viscosity of the product should be high enough so that the product does not run but should be low enough so as to prevent the product from ricocheting off the skin.

The container of the present invention is generally a non-aerosol container which is designed to produce and deliver a product having the physical characteristics of a post-foaming aerosol shave gel. The container, which in combination with the composition of this invention, accomplish this objective deliver a foam upon consumer actuation. Those containers may be ABS (advanced barrier system), Airspray and ATMOS dispensing system.

The ABS dispensing system comprises or consists of a barrier pouch and valve assembly which is inserted into a 1 piece aluminum can and pressure filled through the valve. This assures propellant separation from product and no air contact throughout the life of the product. Actuation allows the compressed gas between the can wall and the barrier pouch to expand and expel product from the container.

The airspray dispensing system comprises or consists of a mousse finger pump that will generate a foam through mechanical action. Product is dispensed as a soft aerated foam created by mixing air from the container headspace with the product concentrate. Foam is produced without the use of any propellant.

The ATMOS dispensing system comprises or consists of a thin walled pleated plastic bottle and valve assembly within a natural rubber sleeve which expands as product is filled through the valve. The contraction of the rubber sleeve when the product is actuated provides the pressure to expel the product from the container.

The present invention is further illustrated by the following drawings.

BRIEF DESCRIPTION OF THE DRAWINGS

FIG. 1 illustrates a first embodiment of an applicator device according to the invention.

DETAILED DESCRIPTION OF THE DRAWINGS

Figure 2:
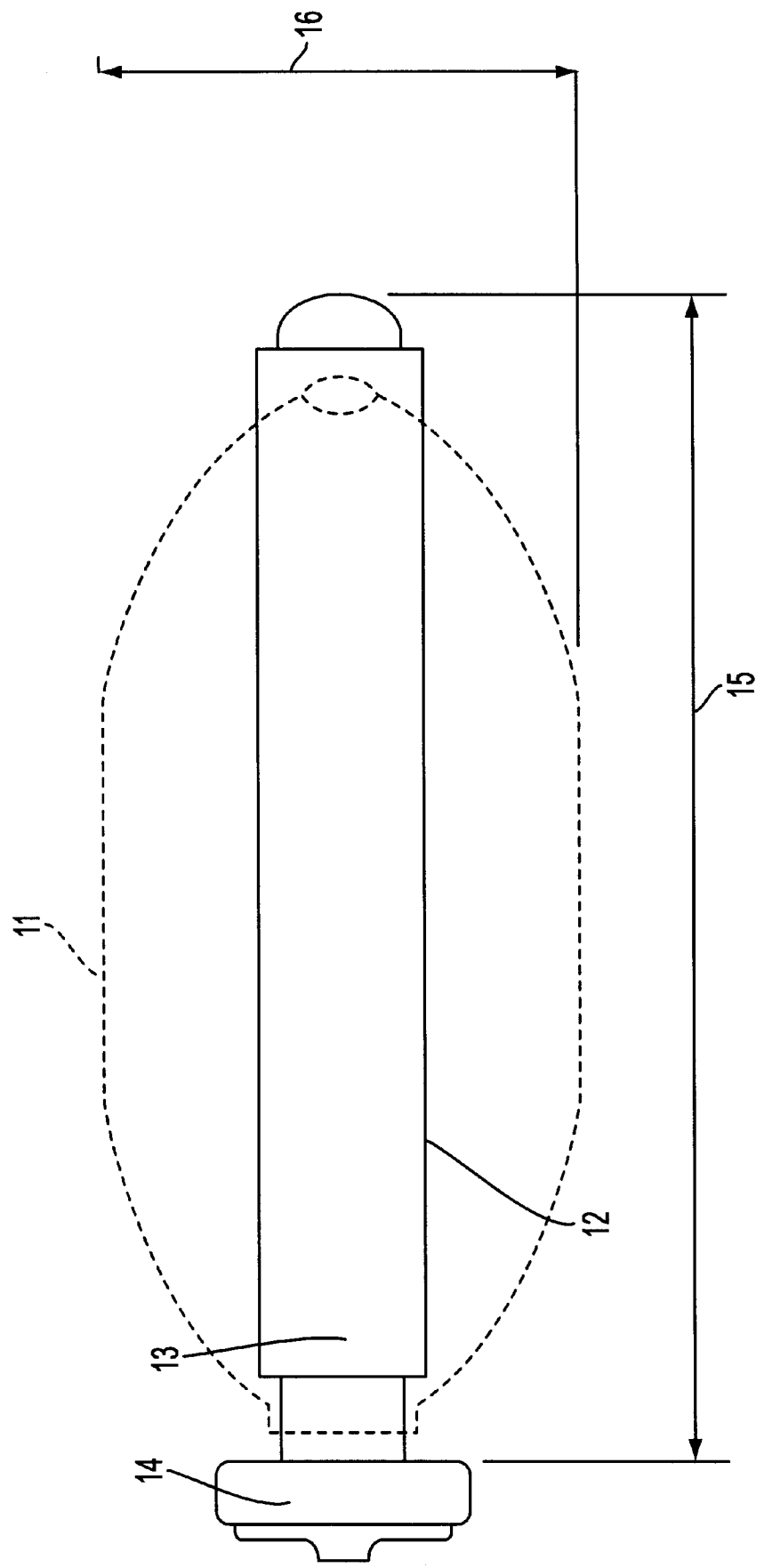
FIG. 2 illustrates a cross sectional view of an empty and a filled device of FIG. 1.

FIG. 1 illustrates an applicator device 1 having an outer container bodywall 2 which is made of natural rubber, and which may be in a form of an energy sleeve. A container 3 is positioned within outer container bodywall 2, and may be in a form of a barrier bag comprised of PET. Container 3 extends to a neck portion, which is surrounded by a portion of bodywall 2 which has an opening through which the neck portion of the container extends to an applicator nozzle 4.

As illustrated in FIG. 1a, applicator nozzle 4 is shown in enlarged view. The neck portion of container 3 extends to and is integral with a container ring member 5. Positioned within the ring member and extending within the neck portion is a spring cup 6 (or valve body). A valve spring 7, which may be made of stainless steel, is positioned and extends within spring cup 6 for reciprocative movement. A valve disk 8 is contained within cup 6 and positioned at a position between an outward extending end of spring 7, and a gasket 9, which extends about and over the spring cup 6 and spring 7 to cover the spring cup and contain the spring within the spring cup. A ferrule 10, preferably comprised of aluminum, engages and secures the gasket, spring, valve disk and cup together.

FIG. 2 illustrates a cross sectional view of the applicator device shown in FIG. 1. The applicator device in expanded form is illustrated by number 11, and in unexpanded or contracted form (i.e., before filling) by number 12. The body wall 2 may exceed 0.805 inches in the area indicated by 13 due to container 3. The outer diameter of ferrule 10 may exceed 0.960 inches at the indent area based on its configuration as shown by 14. The length 15 container 3, shown before filling 12 varies with power assembly size. The diameter 16 of container 3, shown after filling 11 varies with power assembly capacity.

Figure 3:
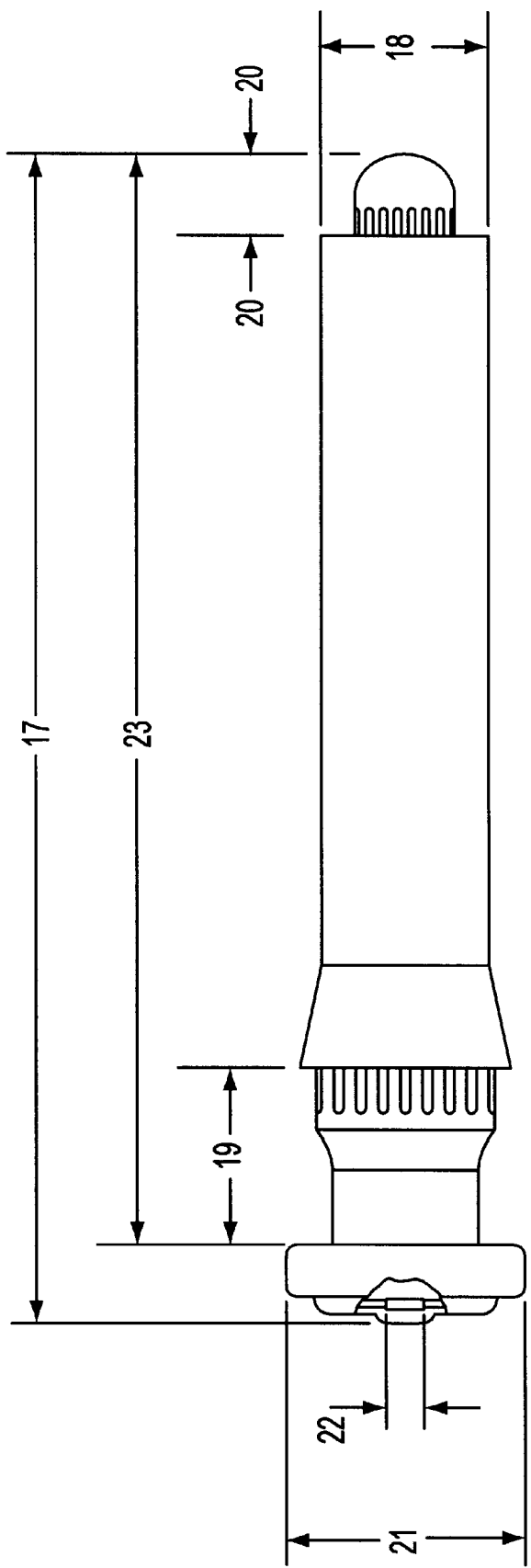
FIG. 3 illustrates a second embodiment according to the invention.

FIG. 3 illustrates another embodiment of the present invention. The overall length (17) may be 5.542 inches. The outer body wall 2 may have a diameter (18) of 0.805 inches. The distance (19) may be 0.75 to 1.0 inches. The distance (20) may be 0.65 inches. The outer diameter (21) of the ferrule may be 0.956 inches (+/−0.004). The inner diameter 22 of the gasket may be 0.153 inches (+/−0.005). The length (23) under the ferrule may be 5.2 inches.

Figure 4:
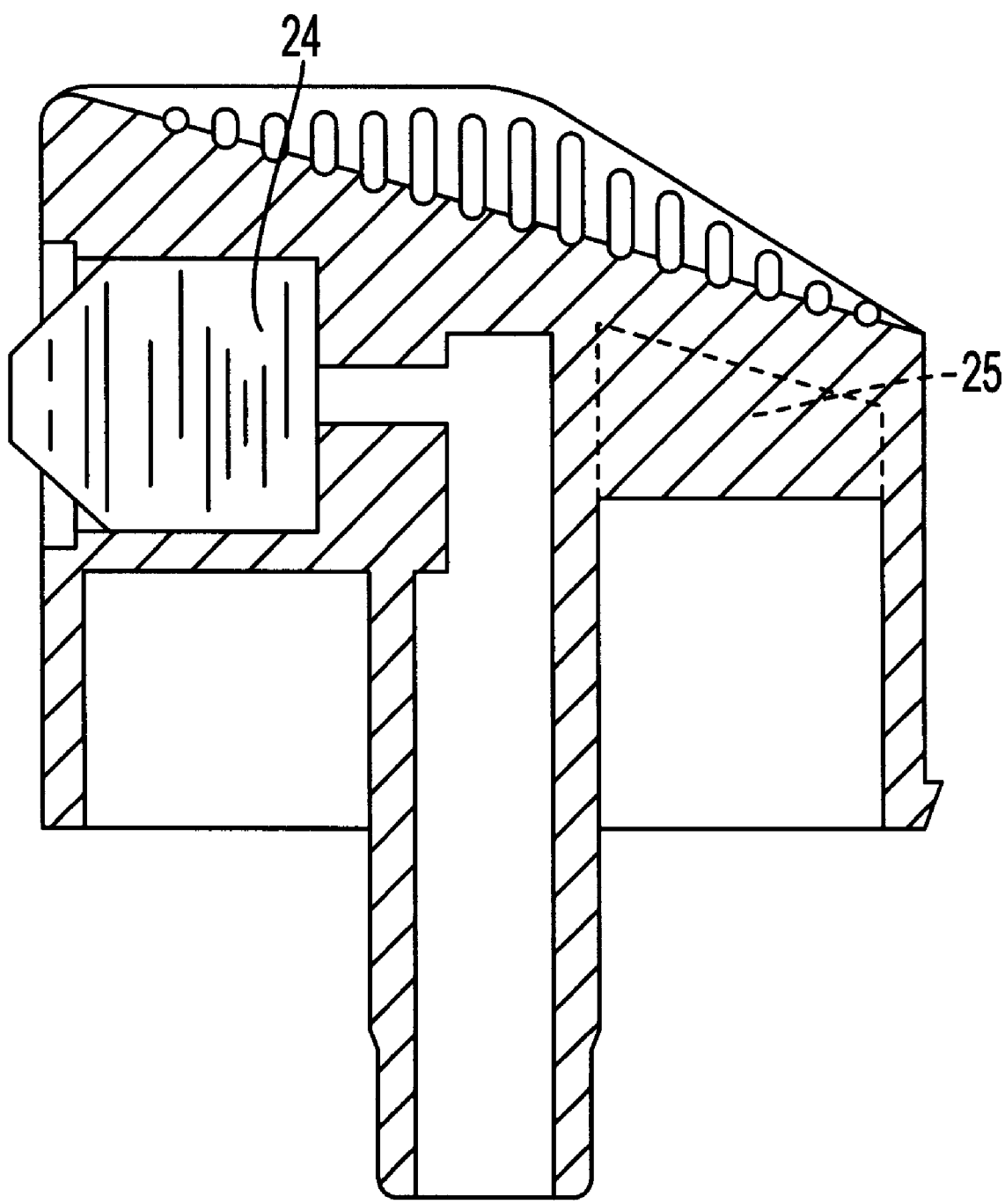
FIG. 4 illustrates an expanded cross sectional view of another embodiment of the applicator nozzle according to the invention.

FIG. 4 illustrates an expanded cross sectional view of another embodiment of the applicator nozzle according to the invention. The applicator nozzle contains an outlet nozzle member 24, which may have orifice sizes such as 0.01, 0.012, and 0.018 inches for releasing the product. The applicator nozzle also contains an actuator shell 25.

Figure 5:
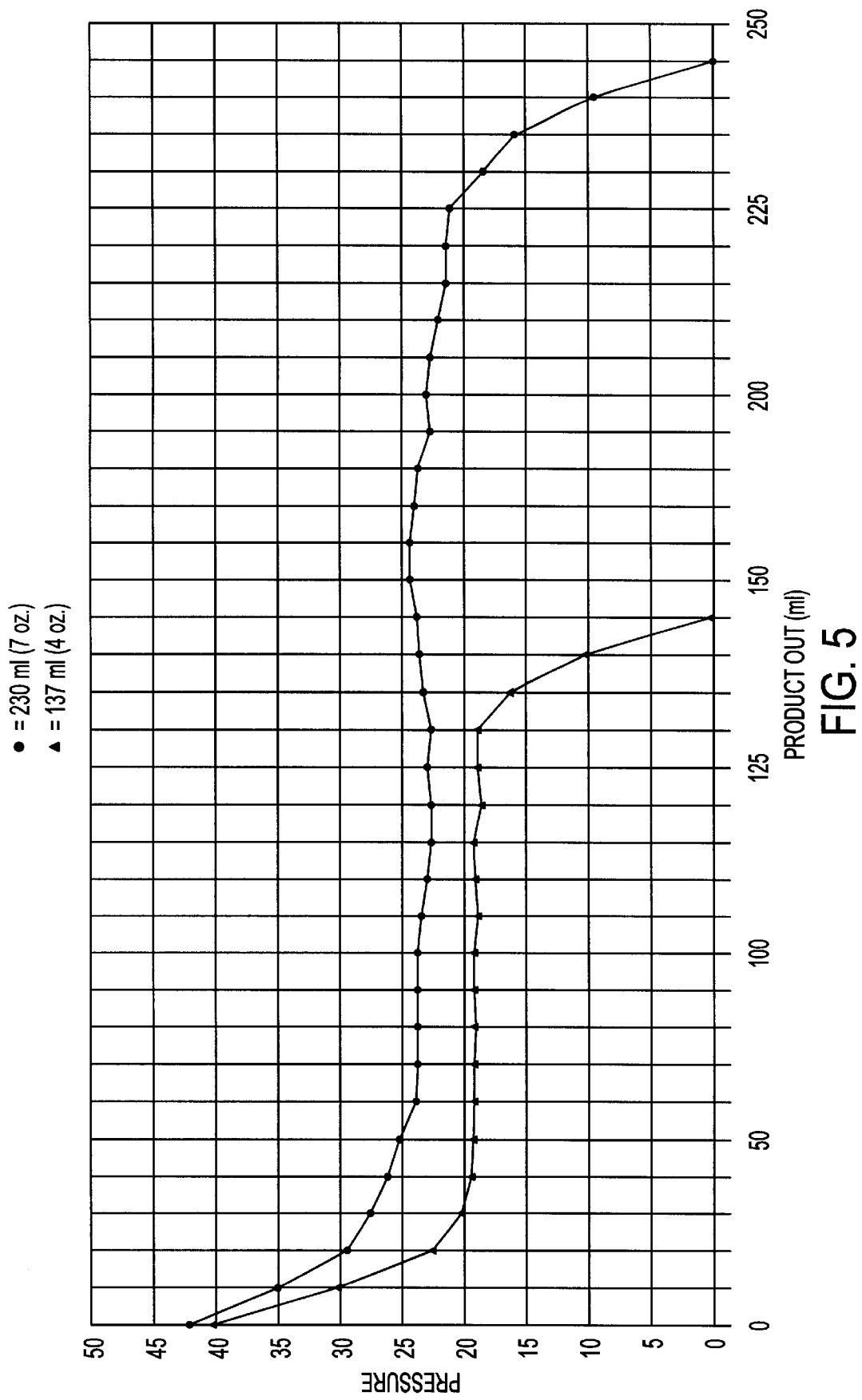
FIG. 5 illustrates a plot of the relationship of pressure employed to product released for the device-containing-product of the invention.

FIG. 5 illustrates a plot of the relationship of pressure employed to product released for the device-containing product of the invention.

The present invention is described further in the following examples which are presented solely for the non-limiting purpose of further illustrating the invention.

EXAMPLES

Example 1

A post-forming bath gel was prepared as follows based on a 125 kilos batch. All parts are by weight unless otherwise specified.

|  | A | 125 Kilos |
|---|---|---|
| Standapol T | 30.00 | 37.50 |
| Jordapon ACI-30G | 10.00 | 12.50 |
| Velvetex AB-45 | 5.00 | 6.25 |
| 2.0% Carbopol ETD-2020 | 38.20 | 47.75 |
| Kathon CG | 0.05 | 0.0625 |
| TEA 99% | 0.80 | 1.00 |
| JAS458AJA | 1.00 | 1.25 |
| FD&C Blue #1 at 1.0% | 0.10 | 18.5625 |
| D-Water | 14.85 | 12.50 |

Kathon CG was added to 2.0% carbopol ETD-2020 and stirred (reduces the viscosity) and then heated to 50° C. with stirring. FD&C Blue #1 at 1.0% was then added followed by Standapol T, Jordapon ACI-30G, and Velvetex AB-45. This mixture was stirred until uniform making sure that carbopol ETD2020 does go into solution. To avoid sticking of the solution to the wall of the vat upon adding carbopol, keep temp. at 50° C. TEA 99% and Distilled water were mixed and stirred and then added to the resultant mixtures prepared first and stirred. JAS458AJA was then stirred for 30 minutes and cooled to room temperature. Base 97%, Isopentane 3.0%. The composition had a pH of 6.30.

It is important the product has 3.0% Isopentane. A mixer is employed to avoid bubbles. In addition, it also is important to add the carbopol to a premix of Standapol T, Jordapon ACI-30G, Velvetex AB-45, Kathon CG, FD&C Blue #1 at 1.0% and Distilled water to avoid the problem of creating a gelled carbopol sticking to the wall of the batch mixer. The viscosity was 3075 cps. The product was further mixed at 20 rpm, using a spindle #3 which resulted in a viscosity of 3825 cps.

Example 2

The following components were combined (based on weight percent) as follows. Witcolate TLS 500 TEA-LAURYL SULFATE (40.00); Velvetex AB-45 COCO-BETAINE (10.00); Citric Acid Monohydrate (0.10); Deionized Water (42.35); Kathon CG, METHYLCHLOROISOTHIAZOLINONE, METHYL-ISOTHIAZOLINONE (0.05), were combined and heated to 60° C. and mixed until clear and uniform (Phase I).

To that mixture, Propylene Glycol (2.00); Glucamate DOE-120 PEG-120 METHYL GLUCOSE DIOLEATE (3.00), were mixed and then heated until a clear uniform liquid is obtained. Phase II was added to Phase I and mix until uniform. The resultant mixture was cooled to 45° C. (Phase II).

Finally, fragrance (2.50) was added and the entire composition (Phase III). While the invention has been illustrated and described with respect to illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

We claim:

1. A dispenser selected from the group consisting of advanced barrier systems, airspray dispensing systems, and a dispensing system comprising a thin walled pleated plastic bottle and valve assembly disposed within an expandable sleeve, containing a post foaming composition at a viscosity of about 500 cps to about 5000 cps in the dispenser, and which dispenser is adapted to dispense a fine stream of the composition as a liquid where the composition comprises at least one surfactant, water at 14.85% (wt), a material which is a volatile liquid at atmospheric pressure, wherein the composition foams upon contact with the skin.

2. A dispenser according to claim 1 wherein the dispenser has an orifice less than about 0.025 inches in diameter.

3. A dispenser according to claim 1 wherein the dispenser has an orifice less than about 0.02 inches in diameter.

4. A dispenser according to claim 2 wherein the dispenser has an orifice less than 0.5 inches in length.

5. A dispenser according to claim 4 wherein the dispenser has an orifice less than 0.25 inches in length.

6. A dispenser according to claim 1 wherein the volatile liquid at atmospheric pressure is a hydrocarbon.

7. A dispenser according to claim 1 wherein the composition contains at least 0.5% w/w of the volatile liquid.

8. A dispenser according to claim 7 wherein the composition contains about 1%–10% w/w of the volatile liquid.

9. A dispenser according to claim 8 wherein the composition contains less than about 7.5% w/w of the volatile liquid.

10. A dispenser according to claim 7 wherein the volatile liquid is selected from the group consisting of propane, n-butane, isobutane, n-pentane, isopentane, halogenated chlorofluoro-carbons and dimethyl ether.

11. A dispenser according to claim 10 wherein the volatile liquid is a 5 carbon aliphatic hydrocarbon.

12. A dispenser according to claim 1 wherein the composition has a viscosity of about 2,000 cps–5,000 cps.

13. A dispenser according to claim 12 wherein the composition contains about 5 (wt) %–50 (wt) % surfactant solids.

14. A dispenser according to claim 13 wherein the composition contains between 10 (wt) %–25 (wt) % surfactant solids.

15. A dispenser according to claim 1 wherein the liquid is dispensed at a rate between 0.5 grams/sec and 10 grams/sec.

16. A dispenser according to claim 15 wherein the liquid is dispensed at a rate between 1 gram/sec and 5 grams/sec.

17. A dispenser according to claim 1 wherein the composition comprises 14.85% (wt) water.

18. A dispenser according to claim 1 wherein the composition comprises 42.35% (wt) water.

* * * * *